United States Patent
Chen

(10) Patent No.: US 12,201,718 B2
(45) Date of Patent: Jan. 21, 2025

(54) GARLIC EXTRACT AND METHOD THEREOF

(71) Applicant: Wei-Hung Chen, Kaohsiung (TW)

(72) Inventor: Wei-Hung Chen, Kaohsiung (TW)

( * ) Notice: Subject to any disclaimer, the term of this patent is extended or adjusted under 35 U.S.C. 154(b) by 371 days.

(21) Appl. No.: 17/598,652

(22) PCT Filed: Apr. 4, 2019

(86) PCT No.: PCT/CN2019/081418
§ 371 (c)(1),
(2) Date: Sep. 27, 2021

(87) PCT Pub. No.: WO2020/199176
PCT Pub. Date: Oct. 8, 2020

(65) Prior Publication Data
US 2022/0168214 A1    Jun. 2, 2022

(51) Int. Cl.
*A61K 8/9794* (2017.01)
*A61Q 19/00* (2006.01)

(52) U.S. Cl.
CPC .......... *A61K 8/9794* (2017.08); *A61Q 19/00* (2013.01); *A61K 2800/85* (2013.01)

(58) Field of Classification Search
CPC ... A61K 8/9794; A61K 2800/85; A61Q 19/00
See application file for complete search history.

(56) References Cited

FOREIGN PATENT DOCUMENTS

| CN | 101243871 A | | 8/2008 |
|---|---|---|---|
| CN | 104177507 A | * | 12/2014 |
| CN | 105614830 A | * | 6/2016 |
| CN | 106344469 A | | 1/2017 |
| CN | 106701851 A | | 5/2017 |
| CN | 109251949 A | * | 1/2019 |
| JP | H07145019 A | | 6/1995 |

(Continued)

OTHER PUBLICATIONS

Cytiva, "Filtering high particulate samples", published online Jul. 11, 2017, webpage accessed Nov. 24, 2023, p. 1-3. (Year: 2017).*

(Continued)

*Primary Examiner* — Gary B Nickol
*Assistant Examiner* — Amelia Nicole Dickens
(74) *Attorney, Agent, or Firm* — Muncy, Geissler, Olds & Lowe, P.C.

(57) ABSTRACT

A method of producing a garlic extract is provided and comprises steps of peeling, sterilization, draining, fermentation, first filtration, and extraction. A plurality of garlics are peeled in the step of peeling. The plurality of garlics are sterilized by utilizing ozonated water in the step of sterilization. The plurality of garlics are drained in the step of draining. The plurality of garlics are fermented in the step of fermentation to get fermented garlic mixture. The fermented garlic mixture is filtered in the step of the first filtration to get a garlic fermentation broth. The garlic fermentation broth is extracted in the step of extraction to get a garlic extract. The present invention uses ozonated water to clean and sterilize the peeled garlic bulbs at normal temperature, so that not only are the garlic fermentation and production stabilized, but the loss of active ingredients in the garlic bulbs is retarded.

2 Claims, 3 Drawing Sheets

(56) References Cited

FOREIGN PATENT DOCUMENTS

| KR | 20110121913 A | | 11/2011 |
|---|---|---|---|
| KR | 10-1861849 B1 | * | 5/2018 |
| TW | 201811309 A | | 4/2018 |
| TW | I655000 B | * | 4/2019 |

OTHER PUBLICATIONS

English machine translation of CN-105614830-A. (Year: 2016).*
English machine translation of Kr- 10-1861849-B1 (Year: 2018).*
English machine translation of TW-I655000-B (Year: 2018).*
English machine translation of CN-104177507-A. (Year: 2014).*
English machine translation of CN-109251949-A. (Year: 2019).*
Zhang, Jinglin et al.; "Effects of Ozone on Sterilization and Major Quality of the Dehydrated Garlic Slices"; Science and Technology of Food Industry, vol. 37, No. 17, Dec. 31, 2016 (Dec. 31, 2016), ISSN:1002-0306 , 5 pages.

* cited by examiner

GARLIC EXTRACT AND METHOD THEREOF

BACKGROUND OF THE INVENTION

1. Field of the Invention

The present invention relates to a method, and in particular, to a method of producing a garlic extract, and the garlic extract produced by the method.

2. Description of the Prior Art

Garlic (*Allium sativum*), also known as Dasuan in Chinese, is one of the five types of pungent vegetables (spring onion, garlic, chives, Chinese scallion ('Xie') and Ferula assafoetida ('Xing Qu')). The underground bulb, also called a garlic knob, can be used for its pungent taste and smell as a condiment and a medicinal material. Both the garlic leaves (also called green garlic or garlic sprouts) and the rachis of garlic (called garlic scapes) are edible as vegetables. Some fermented garlic bulbs are sold on the market as food.

Please refer to Taiwanese Patent Application No. 105129170, which relates to a method of producing a body care composition comprising fermentation of garlic bulbs with bacteria followed by extraction of fermented garlic mixture to obtain a garlic extract. The garlic extract can be used for human skin care, and can be added to general care products.

The prior art is to ferment garlic bulbs directly. Since the obtained fermented garlic mixture is not sterilized, the quality of garlic fermentation is unstable, resulting in a significant reduction in the anti-inflammatory and care effects of the product.

In addition, the fermented garlic mixture contains many solid components, i.e. solid garlic, after fermentation. The solid components are prone to get burned and create a burnt smell in the vessel during the extraction process, resulting in defects in the garlic extract so that the garlic extract fails to meet product standards.

As can be seen from the above description, although the prior art reveals a method of producing garlic extracts, it still has the following deficiencies in practice:

1. It is difficult to control the quality of fermentation.

It is easy for other bacteria to adhere to the garlic bulbs during the process of peeling, and these bacteria will affect the garlic fermentation, resulting in an uncontrollable quality of the garlic fermentation.

2. There is a burnt smell.

The solid components of the fermented garlic mixture are prone to get burnt and carbonized during distillation and extraction, resulting in a burnt smell of the garlic extract.

3. There is a strong garlic odor.

The fermented plurality of garlics produce a large amount of allicin, which creates a garlic odor. Some consumers resist the garlic odor and will refuse to use products made from garlic fermentation broth.

Therefore, it is desirable for those skilled in the art to stabilize the fermentation of garlic and improve the flavor of the garlic extract.

SUMMARY OF THE INVENTION

To address the deficiencies of the prior art, one of the objectives of the present invention is to provide a garlic extract and a method thereof.

In order to achieve the above-mentioned objective, the present invention provides a method of producing a garlic extract, comprising the following steps:

peeling, wherein a plurality of garlics are peeled;

sterilization, wherein the plurality of garlics are sterilized by utilizing ozonated water;

draining, wherein the plurality of garlics are drained;

fermentation, wherein the plurality of garlics are fermented to get fermented garlic mixture;

first filtration, wherein the fermented garlic mixture is filtered to get a garlic fermentation broth; and extraction, wherein the garlic fermentation broth is extracted to get a garlic extract.

In some embodiments, in the above-mentioned step of sterilization, the concentration of the ozonated water is between 0.3 ppm and 0.7 ppm.

In some embodiments, in the above-mentioned step of sterilization, the plurality of garlics are soaked in the ozonated water for 5-15 minutes.

In some embodiments, in the above-mentioned step of fermentation, the plurality of garlics are fermented by utilizing *Acetobacter Pasteurianus*, water and sugar.

In some embodiments, in the above-mentioned step of fermentation, the weight ratio of the plurality of garlics, the sugar, the water and said *Acetobacter Pasteurianus* is 180:30:280:0.1.

In some embodiments, in the above-mentioned step of fermentation, an aerobic fermentation is performed first, followed by an anaerobic fermentation.

In some embodiments, in the above-mentioned step of filtration, filtration with a coarse mesh is performed first, followed by filtration with a fine mesh.

In some embodiments, in the above-mentioned step of extraction, the garlic fermentation broth is extracted by performing distillation at an extraction temperature of 80° C.-120° C.

In some embodiments, the above-mentioned garlic extract and the method thereof further comprise a step of second filtration following the step of extraction, whereby the garlic extract is filtered.

In some embodiments, the above-mentioned garlic extract and the method thereof further comprise a step of deodorization following the step of extraction, whereby the garlic extract is filtered by utilizing activated carbon.

The other objective of the present invention is to provide a garlic extract, wherein the garlic extract is produced by the above-mentioned method of producing garlic extracts, and is suitable for being applied to a surface layer of skin.

The feature of the present invention is that by using ozonated water at normal temperature to clean and sterilize the peeled garlic bulbs, not only is the garlic fermentation stabilized, but the loss of active ingredients in the garlic bulbs is retarded. Also, by separating the solid components from the fermented garlic mixture through filtration, the scorching of the solids and the consequent burnt smell can be avoided during distillation and extraction.

DETAILED DESCRIPTION OF THE PREFERRED EMBODIMENTS

Three embodiments of the invention will be introduced with reference to the accompanying drawings to demonstrate the features and technical content of the invention. It should be noted that, similar components are represented by the same number in the detailed description.

Figure 1:
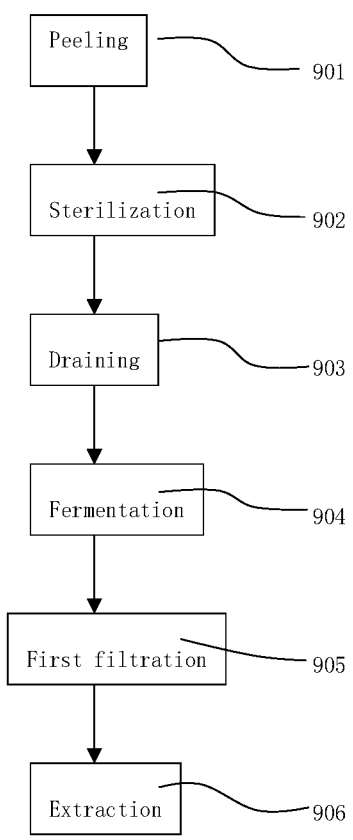
FIG. 1 is a flowchart showing a garlic extract and method thereof in accordance with a first embodiment of the present invention.

FIG. 1. shows a method of producing a garlic extract in accordance with the first embodiment of this invention, wherein the method of producing a garlic extract comprised the following steps: a peeling step (901), a sterilization step (902), a draining step (903), a fermentation step (904), a first-filtration step (905) and an extraction step (906).

Firstly, the peeling step (901) was performed to peel a plurality of garlics. The membrane on the outer surface of the plurality of garlics can be peeled with a garlic peeling machine. The variety of the plurality of garlics is Great Leaf Black. According to certain embodiments, other types of garlic bulbs can be used and may vary from implementation to implementation. Preferably, a commercially available garlic peeling machine can be used to peel the plurality of garlics. According to certain embodiments, other methods can be used to peel the membrane of the plurality of garlics and may vary from implementation to implementation.

Next, the sterilization step (902) was performed, wherein the plurality of garlics were sterilized by using ozonated water with a concentration of 0.3-0.7 ppm, and the plurality of garlics were soaked in the ozonated water for 5-15 minutes. Ozone ($O_3$), with a stronger reactivity than oxygen ($O_2$), can be dissolved in water and form the ozonated water which has a killing effect on biological cells, so the ozonated water has an antiseptic effect.

In the sterilization step (902), the peeled garlics was soaked in the ozonated water to eliminate the bacteria attached to the surface of the garlic bulbs. Preferably, the plurality of garlics were soaked in ozonated water of 0.5 ppm for 10 minutes. According to certain embodiments, the concentration of the ozonated water and the duration of the soaking can be adjusted according to the process conditions, and may vary from implementation to implementation.

Next, the draining step (903) was performed to drain the plurality of garlics sterilized by the ozonated water, preferably by shade drying or breeze drying, to remove the ozonated water from the surface of the garlic bulbs at room temperature, which could prevent the residual ozonated water from affecting the subsequent fermentation process as the ozone in the ozonated water was dissipated in the air during the draining process.

Next, the fermentation step (904) was performed to ferment the drained plurality of garlics and obtain fermented garlic mixture. The plurality of garlics were fermented by utilizing *Acetobacter Pasteurianus*, water and sugar. The strain of *Acetobacter Pasteurianus* was BCRC14145, which is commercially available. Since it is a known strain that is commercially available to the public, the *Acetobacter Pasteurianus* used in the present invention was not deposited.

The weight ratio of said plurality of garlics, said sugar, said water and said *Acetobacter Pasteurianus* was 180:30:280:0.1. For example, 180 kg of said garlic bulbs, 30 kg of said sugar, 280 kg of said water and 100 g of said *Acetobacter Pasteurianus* were added to the fermentation vessel.

In the fermentation step (904), an aerobic fermentation was performed first, followed by an anaerobic fermentation. For example, the fermentation of the plurality of garlics lasted 16 weeks in total; the fermentation vessel was left uncovered from week 0 to week 4 to allow the fermented garlic mixture to breathe, and the fermented plurality of garlics was stirred for aerobic fermentation; the fermentation vessel was then sealed from week 5 to week 16 to avoid contact between the fermented garlic mixture and the ambient air for anaerobic fermentation.

In the fermentation step (904), the brix, pH and odor of the fermented garlic mixture in the fermentation vessel changed. The plurality of garlics sank to the bottom of the fermentation vessel late in the fermentation step (904).

Next, the first-filtration step (905) was performed to filter the fermented garlic mixture to obtain a garlic fermentation broth. Filtration with a coarse mesh was performed first, followed by filtration with a fine mesh. The pore size of the coarse mesh was between 1 mm and 5 mm, and the pore size of the fine mesh was between 0.1 mm and 0.5 mm. According to certain embodiments, filter of other sizes, or other methods of filtration can be used to separate the solid from the liquid of the fermented garlic mixture, for example, a centrifuge can be used to separate the solid from the liquid which is taken as the garlic fermentation broth, and may vary from implementation to implementation.

Finally, the extraction step (906) was performed to extract the garlic fermentation broth and obtain a garlic extract. The distillation method was used to extract the garlic fermentation broth at an extraction temperature of 80° C.-120° C., preferably, the extraction temperature was 90° C., and the liquid obtained after distillation was the garlic extract. Since the solid components of the fermented garlic mixture had been removed in the step of first filtration, no scorching or burnt smell was created during the distillation. During the distillation and extraction process, the extracts obtained 10 minutes after the beginning and 10 minutes before the end can be discarded to stabilize the quality of the garlic extract. According to certain embodiments, the time to obtain the garlic extract can be determined according to the extraction status, and may vary from implementation to implementation.

The obtained garlic extract can be applied to a skin surface directly and provides antiseptic and care effects for the skin. Preferably, additives can be added into the garlic extract to form a care product for human skin. The additive can be one selected from the group consisting of water, aloe vera, collagen, L-C, hyaluronic acid, peptides, lecithin, tranexamic acid, γ-PGA (polyglutamic acid), gea (natural grape seed antioxidant), PC (lecithin-phosphatidylcholine), resveratrol, glutamate fermentation product GABA, D-ribose, etc., and combinations thereof. The above-mentioned care materials can also be added with excipients selected from the group consisting of lactose, starch, silica, microcrystalline cellulose, carboxymethyl cellulose, talc, magnesium stearate and combinations thereof. The above-mentioned care materials can also be added with lubricant additives selected from the group consisting of glycerin, vegetable oil, mineral oil, essential oil, and combinations thereof. The above-mentioned care materials can be in the form of gel, liquid, emulsion, oil, powder, ointment or solid. Since the technical means of adding other skin-care materials to form care products for human skin is a known technology and is widely used in commercial products, it will not be described here in details.

Garlic bulbs contain allicin, which has antibacterial, antiviral, immune-boosting, cholesterol-lowering and anticoagulant effects, and is also the main source of garlic bulbs' pungent flavor. However, the content of allicin in fresh and undamaged garlic is quite limited, because allicin is derived from the decomposition of alliin in the cytoplasm by alliinase located in the cell wall of garlic bulbs. There are not significant exposure of the two substances to each other when the cell walls of garlic bulbs are intact; and allicin is only produced in large quantities when these two substances come into contact as the cell structure of the garlic bulbs is destroyed.

In the present invention, garlic bulbs were fermented with *Acetobacter Pasteurianus*, which promoted the contact of alliinase and alliin in garlic bulbs during the fermentation process to further form a large amount of allicin, which can also be converted to ajoene. All the allicin and ajoene were preserved in the fermentation vessel without loss before they were extracted by distillation-extraction technology. Among them, allicin has strong antibacterial and anti-inflammatory effects, and can be formulated into a proper external liniment and applied to human skin to solve various annoying skin problems.

For example, the garlic extract can be used to make a lotion, which comprises the following ingredients: 10%-50% of garlic extract, 0.1%-2% of lecithin, 0.5%-5% of oil, 10%-65% of aloe vera liquid and 20% of water. The above-mentioned percentage is weight percentage. According to certain embodiments, the materials should be proportioned according to the application of the product and may vary from implementation to implementation.

It is worth mentioning that the garlic extract contains large quantities of allicin, which is inherently antiseptic, and hence it can be encapsulated and preserved without spoiling. The allicin in the garlic extract also has an anti-inflammatory effect, reducing inflammation of wounds and assisting in faster wound healing.

Figure 2:
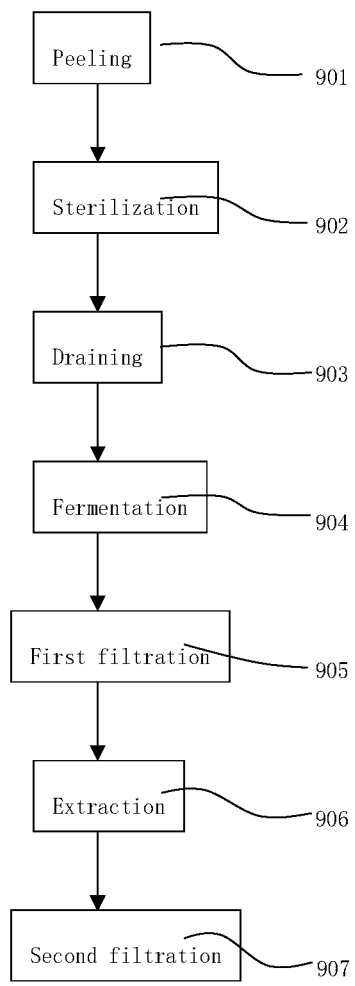
FIG. 2 is a flowchart showing a garlic extract and method thereof in accordance with a second embodiment of the present invention.

FIG. 2. shows a method of producing a garlic extract in accordance with a second embodiment of this invention, which is similar to the first one. The same features are not described in details here. The difference lies in that the method of producing a garlic extract further comprised a second-filtration step (907) following the extraction step (906) to filter the garlic extract.

The second-filtration step (907) was used to filter some contaminants from the extraction process. For example, solid contaminants, such as dust in the air or dirt in the distillation vessel, can affect the visual appearance of the liquid when dropped into the garlic extract. The step of second filtration was a protective measure to separate the solid components from the garlic extract, thereby improving the clarity of the garlic extract, and providing more peace of mind to users of the product. According to certain embodiments, the step of second filtration is not required if the environment is clean enough so that the garlic extract is not contaminated with dust, and it shall not be limited by the example of the second embodiment.

Figure 3:
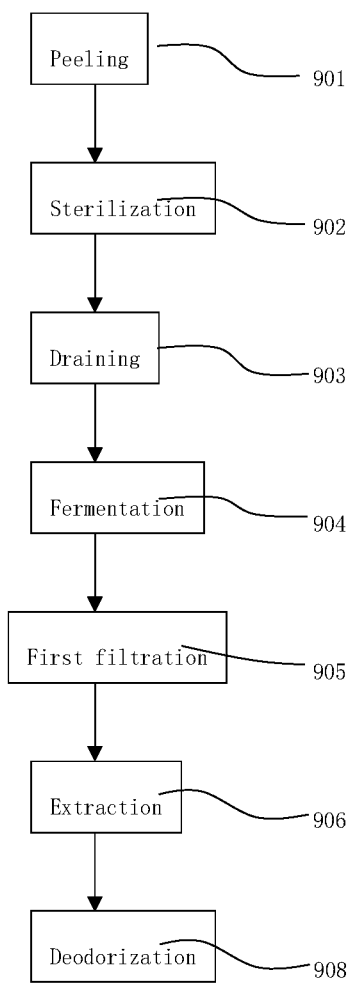
FIG. 3 is a flowchart showing a garlic extract and method thereof in accordance with a third embodiment of the present invention.

FIG. 3. shows a garlic extract and method thereof in accordance with a third embodiment of this invention, which is similar to the first one. The same features are not described here in details. The difference lies in that the method of producing a garlic extract further comprised a deodorization step (908) following the extraction step (906) to filter the garlic extract using activated carbon.

Allicin contained in the garlic extract gives off an odor of garlic bulbs. The pungent garlic odor can be removed by filtering the garlic extract with an activated carbon filter cartridge. The activated carbon absorbed the garlic odor of the garlic extract, so that the garlic flavor was significantly reduced or disappeared, which would further enhance consumers' willingness to use products made by the garlic extract. According to certain embodiments, the deodorization step (908) may be omitted, and may vary from implementation to implementation.

As can be seen from the above description, the garlic extract and the method thereof in the present invention do have the following effects:

1. no burnt smell:

In the present invention, the first-filtration step (905) is performed before the extraction step (906) to filter the fermented garlic mixture with a mesh or a filter cartridge to remove the solid components therein, which can effectively prevent the burning of the solids in the fermented garlic mixture and a consequent burnt smell in the extraction step (906), which further affects the quality of the garlic extract.

2. stable fermentation quality:

The fermentation step (904) of the present invention comprises quantified components, fixed duration of garlic fermentation, and aerobic fermentation followed by anaerobic fermentation, all of which can effectively stabilize the quality of garlic fermentation. Furthermore, in the sterilization step (902), ozonated water is used to eliminate bacteria attached to the surface of the garlic bulbs, which helps to make the fermentation process of the plurality of garlics in better control.

3. improvement on the garlic odor:

In the deodorization step (908), an activated carbon filter cartridge can be used to adjust the garlic odor of the garlic extract, which will help to avoid situations where the consumers refuse to use products made from the garlic extract because of the strong garlic odor.

In summary, the present invention uses ozonated water to sterilize the garlic bulbs at room temperature, so that the loss of active ingredients in the garlic bulbs is retarded; filtration is carried out to filter the solid components in the fermented garlic mixture and avoid a burnt smell during the extraction; and also, an activated carbon filter can be used accordingly to filter the garlic extract to reduce the odor of fermentation and allicin. Therefore, the objectives of the invention can indeed be achieved.

The above-mentioned are merely embodiments of the present invention, and do not limit the protection scope of the invention, i.e., any mild equivalent variation and modification made in accordance with the protection scope of the present invention and the description of the invention shall remain within the scope of the present invention.

What is claimed is:

1. A method of producing a garlic extract, comprising the following steps:

peeling, wherein a plurality of garlics are peeled;

sterilization, wherein the plurality of garlics are sterilized by utilizing ozonated water, a concentration of the ozonated water is between 0.3 ppm and 0.7 ppm, and the plurality of garlics are soaked in the ozonated water for 5-15 minutes;

draining, wherein the plurality of garlics are drained by shade drying or breeze drying at room temperature to remove the ozonated water from the surface of the garlics;

fermentation, wherein the plurality of garlics are fermented by utilizing *Acetobacter pasteurianus*, water and sugar to get a fermented garlic mixture, wherein a weight ratio of the plurality of garlics, the sugar, the water and the *Acetobacter pasteurianus* is 180:30:280:0.1, wherein an aerobic fermentation is performed first, followed by an anaerobic fermentation, wherein in the early ¼ of a fermentation cycle, the fermented garlic mixture is ventilated, and the fermented garlic mixture is stirred to carry out the aerobic fermentation, and in the late ¾ of the fermentation cycle, the fermented garlic mixture is sealed to prevent the fermented garlic mixture from contacting with outside air for anaerobic fermentation;

first filtration, wherein the fermented garlic mixture is filtered with a coarse mesh first and then a fine mesh to get a garlic fermentation broth, wherein a pore size of the coarse mesh is between 1 mm and 5 mm, and a pore size of the fine mesh is between 0.1 mm and 0.5 mm;

extraction, wherein the garlic fermentation broth is extracted using a distillation method to get a garlic extract at an extraction temperature of 80° C.-120° C., wherein the garlic extract obtained in the first 10 minutes and the last 10 minutes during the distillation is discarded; and deodorization, wherein the garlic extract is filtered by utilizing an activated carbon filter cartridge.

2. The method of producing the garlic extract as recited in claim 1, further comprising a step of second filtration following the step of extraction, whereby the garlic extract is filtered.

\* \* \* \* \*